United States Patent
Nita et al.

[11] Patent Number: 5,951,539
[45] Date of Patent: Sep. 14, 1999

[54] OPTIMIZED HIGH PERFORMANCE MULTIPLE COIL SPIRAL-WOUND VASCULAR CATHETER

[75] Inventors: Henry Nita, Milpitas; Lex P. Jansen, Pleasanton; Peter Kyone Park, Santa Clara; Gene Samson, Milpitas; Erik T. Engelson, Menlo Park; Jeffrey A. Sarge, Fremont, all of Calif.

[73] Assignee: Target Therpeutics, Inc., Fremont, Calif.

[21] Appl. No.: 08/995,088

[22] Filed: Dec. 19, 1997

Related U.S. Application Data

[63] Continuation-in-part of application No. 08/872,215, Jun. 10, 1997.

[51] Int. Cl.$^6$ .................................................. A61M 25/00
[52] U.S. Cl. ............................................ 604/526; 604/524
[58] Field of Search .................................. 604/202, 200, 604/264, 96, 95

[56] References Cited

U.S. PATENT DOCUMENTS

| | | |
|---|---|---|
| 243,396 | 6/1881 | Pfarre . |
| 2,211,975 | 8/1940 | Hendrickson . |
| 2,437,542 | 3/1948 | Krippendorf . |
| 3,174,851 | 3/1965 | Buehler et al. . |

(List continued on next page.)

FOREIGN PATENT DOCUMENTS

| | | |
|---|---|---|
| 0098100 | 1/1984 | European Pat. Off. . |
| 0661072 | 7/1995 | European Pat. Off. . |
| 2613231 | 10/1988 | France . |
| 0421650 | 4/1991 | France . |
| 3642107 | 6/1987 | Germany . |
| 2-283346 | 11/1990 | Japan . |
| 3-023830 | 1/1991 | Japan . |
| 5-56910 | 3/1993 | Japan . |
| 5-220225 | 8/1993 | Japan . |
| WO 92/07507 | 5/1992 | WIPO . |
| WO 93/05842 | 4/1993 | WIPO . |
| WO 93/15785 | 8/1993 | WIPO . |
| WO 96/33763 | 10/1996 | WIPO . |

*Primary Examiner*—Wynn Wood Goggins
*Assistant Examiner*—N. Kent Gring
*Attorney, Agent, or Firm*—Morrison & Foerster LLP

[57] ABSTRACT

This invention is a surgical device. In particular, it is a catheter suitable for accessing a tissue target within the body, typically a target which is accessible through the vascular system. Central to the invention is the use of at least pair of wound or counterwound reinforcing members situated within the wall of the catheter body in such a way to achieve a catheter having an exceptionally thin wall, excellent kink-resistance, and controlled stiffness. The catheter assembly desirably is constructed of: (a) an inner, polymeric, lubricious liner, (b) a first, helically wound coil extending over at least the more distal portions of the inner liner but preferably for most of the length of the catheter, (c) a second, helically wound coil exterior to the first coil, located at least on the more proximal portion of the assembly but preferably for most of the length of the catheter, preferably wound in a direction opposite to the first coil, (d) optionally, one or more helically wound coils placed on the proximal and mid-section of the assembly, and (e) one or more polymeric layers variously exterior to the second coil and interior to the first coil. Preferably, the coils are wound from metallic ribbons or wireshaving a relatively constant pitch of from 10°–15° of the central catheter axis. Further polymeric layers may also be placed between the outer polymeric covering and various and the helically wound coils. The outer polymeric covering may be composed of a series of different polymeric compositions to provide suitably differing flexibilities along the length of the assembly. The catheter assembly is quite easy to produce. The helically wound coils may be bound to the assembly via the use of radio-opaque bands or coils and may be continuously wound from a single member. The distal-most portion of the catheter assembly is very flexible but highly kink resistant. Optionally, the invention includes a catheter in which only the more distal catheter section incorporates multiple coil stiffener members.

19 Claims, 14 Drawing Sheets

U.S. PATENT DOCUMENTS

| | | |
|---|---|---|
| 3,351,463 | 11/1967 | Rozner et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |
| 4,430,083 | 2/1984 | Ganz et al. . |
| 4,484,586 | 11/1984 | McMickle et al. . |
| 4,516,972 | 5/1985 | Samson . |
| 4,657,024 | 4/1987 | Coneys . |
| 4,676,229 | 6/1987 | Krasnicki et al. . |
| 4,737,153 | 4/1988 | Shimamura et al. . |
| 4,739,768 | 4/1988 | Engelson . |
| 4,806,182 | 2/1989 | Rydell et al. . |
| 4,832,681 | 5/1989 | Lenck . |
| 4,899,787 | 2/1990 | Ouchi et al. . |
| 4,981,478 | 1/1991 | Evard et al. . |
| 4,985,022 | 1/1991 | Fearnot et al. . |
| 5,037,404 | 8/1991 | Gold et al. . |
| 5,057,092 | 10/1991 | Webster, Jr. . |
| 5,069,674 | 12/1991 | Fearnot et al. . |
| 5,176,660 | 1/1993 | Truckai . |
| 5,178,158 | 1/1993 | de Toledo . |
| 5,180,376 | 1/1993 | Fischell . |
| 5,184,627 | 2/1993 | de Toledo . |
| 5,217,482 | 6/1993 | Keith . |
| 5,222,949 | 6/1993 | Kaldany . |
| 5,248,305 | 9/1993 | Zdrahala . |
| 5,313,967 | 5/1994 | Lieber et al. . |
| 5,454,795 | 10/1995 | Samson . |

OPTIMIZED HIGH PERFORMANCE MULTIPLE COIL SPIRAL-WOUND VASCULAR CATHETER

RELATED APPLICATION

This is a continuation-in-part of U.S. patent application Ser. No. 08/872,215 filed Jun. 10, 1997 entitled "OPTIMIZED HIGH PERFORMANCE SPIRAL-WOUND VASCULAR CATHETER", pending.

FIELD OF THE INVENTION

This invention is a surgical device. In particular, it is a catheter suitable for accessing a tissue target within the body, typically a target which is accessible through the vascular system. Central to the invention is the use of at least pair of wound or counterwound reinforcing members situated within the wall of the catheter body in such a way to achieve a catheter having an exceptionally thin wall, excellent kink-resistance, and controlled stiffness. The catheter assembly desirably is constructed of: (a) an inner, polymeric, lubricious liner, (b) a first, helically wound coil extending over at least the more distal portions of the inner liner but preferably for most of the length of the catheter, (c) a second, helically wound coil exterior to the first coil, located at least on the more proximal portion of the assembly but preferably for most of the length of the catheter, preferably wound in a direction opposite to the first coil, (d) optionally, one or more helically wound coils placed on the proximal and mid-section of the assembly, and (e) one or more polymeric layers variously exterior to the second coil and interior to the first coil. Preferably, the coils are wound from metallic ribbons or wires having a relatively constant pitch of from 10°–15° of the central catheter axis. Further polymeric layers may also be placed between the outer polymeric covering and various and the helically wound coils. The outer polymeric covering may be composed of a series of different polymeric compositions to provide suitably differing flexibilities along the length of the assembly. The catheter assembly is quite easy to produce. The helically wound coils may be bound to the assembly via the use of radio-opaque bands or coils and may be continuously wound from a single member. The distal-most portion of the catheter assembly is very flexible but highly kink resistant.

Optionally, the invention includes a catheter in which only the more distal catheter section incorporates multiple coil stiffener members.

BACKGROUND OF THE INVENTION

Catheters are increasingly used to access remote regions of the human body and, in doing so, to deliver diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. Size, kink-resistance, trackability (the ability to follow a guidewire into and through tortuous vasculature), and flexibility are the physical parameters principally contributing to the utility of the class of catheters.

One such treatment of circulatory system diseases is via angioplasty (PCTA). Such a procedure uses catheters having balloons on their distal tips. It is similarly common that those catheters are used to deliver a radiopaque agent to the site in question prior to the PCTA procedure to view the problem prior to treatment.

Often the target to be accessed by catheter is within a soft tissue such as the liver or the brain. These are difficult sites to reach. The catheter is usually introduced through a large artery such as those found in the groin or in the neck and then must be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above. Yet, at the same time, the catheters must not cause significant trauma to the blood vessel or to the surrounding tissue during their passage. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have supple distal ends which are carried by blood flow to the target site.

The invention combines one or more polymeric tubes with one or more spirally wound ribbons to control the stiffness of the resultant catheter section or body. The construction technique allows the production of catheters having very small diameters but which are very flexible and kink resistant.

The use of ribbons or wires in winding a catheter body is not a novel concept. Typical background patents are discussed below.

Multi-Wrap Catheters

There are a number of catheters discussed in the literature which utilize catheter bodies having multiply wrapped reinforcing material. These catheters include structures having braided bands or ones in which the spirally wound material is wound in one direction and the following layer or layers are wound in the other.

Krippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in a region other than in the body's periphery or in its soft tissues.

Similarly, U.S. Pat. No. 3,416,53 1, to Edwards, shows a catheter having "braiding-edge" walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multi-layered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and the filaments are wound at a tension of about 250,000 lb./in.$^2$ (of cross-section) or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer, Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to de Toledo, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,567,024, to Coneys, shows a catheter which employs a set of helical strips within the wall of the catheter. However, the helical strips are of a radiopaque material, e.g., fluorinated ethylene-propylene (FEP). It is not clear that the blended radiopaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube. There is no suggestion within the patent that the interior coil be made to adhere to the outer tubular sheath.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath (40) of Teflon that extends from the proximal end (12) to the distal end (14) of the device. The overlying sheath (40) may extend or overhang at the proximal or the distal end of the catheter. The distal tip portion (13) is said to be "flexible, soft, and floppy". The PCT Published Application corresponding to this U.S. Pat. No. 5,184,627 shows a guidewire suitable for infusion of medicaments to various sites along the guidewire. The guidewire is made up of a helically wound coil having a polyimide sheath enclosing its proximal portion and a Teflon sheath tightly covering the entire wire coil.

U.S. Pat. No. 5,313,967, to Lieber et al., shows a medical device a portion of which is a helical coil which, apparently, may include an outer plastic sheath in some variations. Apparently, a secondary helix of a somewhat similar design, in that it is formed by rotating a flat wire or the like along its longitudinal axis to form a screw-like configuration, is included within the helical coil to provide axial pushability and torque transmission.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold."

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultra-thin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . . ". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a medical probe used with an endoscope or for some other device used to stimulate the heart. The device appears to be a helix having a spacing between 0 and 0.25 mm (See page 4, line 20) preferably rectangular in cross section (See Page 4, Line 1) and of a multi-phase alloy such as MP35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-kinking Configurations

U.S. Pat. No. 5,222,949, to Kaldany, describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher degree of cross-linking.

European Patent Application No. 0,421,650-A1 describes a method for producing a catheter from a roll of polymer film while incorporating other materials such as tinfoil elements or the like.

None of the documents cited above provides a structure required by the disclosure and claims recited below.

SUMMARY OF THE INVENTION

This invention is a catheter having two or more spirally wound reinforcement ribbons or wires, preferably stainless steel, typically placed between an outer polymeric covering and an inner lubricious polymeric liner, sometimes interspersed with other filler layers or sections.

The preferred stiffener ribbons are single strands of ribbon helically wound first in a single direction and preferably further wound back over at least a proximal portion of the catheter to form a region of double thickness. The ribbons may be metallic and most desirably are of a stainless steel or super-elastic alloy, but may be of other materials. Most preferred is a catheter having coils with a pitch of 10°–15° to the catheter axis. The helically wound coils may be in contact either with the outer polymeric covering or the inner polymeric liner. The distal-most end of each of the helical windings may be held in place by a radio-opaque band or coil. The inner polymeric liner is preferably of a lubricious material which may be extruded or cast in thin sections. The outer polymeric covering is preferably constructed of a series of polymeric materials having increasing flexibility as the distal end of the catheter assembly is approached.

Other variants of the invention include the use of round, oval, and square wires in the helical coils as well as the use of more than two helically wound coil layers in the catheter assembly, most desirably in the proximal end and mid-section of the assembly.

Another variation of the inventive catheter involves the use of multiple helically wound coils wound in the same direction but either off-set from each other or having different pitches.

Wise choices of materials permit this inventive catheter to be of a smaller overall diameter with a superior kink resistance and surprising flexibility. One variation of this invention involves telescoping catheters with an inner catheter of this construction, perhaps with an inner guidewire. The catheter may be wholly constructed of materials which are stable to radioactive sterilization procedures.

DESCRIPTION OF THE INVENTION

This invention is a thin-walled, highly flexible, kink-resistant catheter assembly. It is a composite device having multiple sections as viewed along the axis of the catheter with different or varying stiffnesses. It has an inner-most layer, preferably polymeric, and most preferably of a lubricious polymer such as polytetrafluoroethylene. The inner polymeric layer preferably extends from the proximal end of the catheter assembly to the distal end. The continuity of the inner layer is a matter of manufacturing convenience and efficiency. The design includes at least a pair of helically wound stiffener members coaxial with both the polymeric outer layer and the inner lubricious liner. The stiffener members may be wound in the same direction or counter-wound and may be variously round, oval, or square wire or may be ribbon. Additional layers of polymeric material may be placed variously between the coils and the polymeric outer layer and between the coils and the inner polymeric liner if so desired. The construction of the catheter desirably provides radially situated polymeric columns through the interstices between the turns of the coils. The multiple layers of coil and the internal configuration of the polymer are believed to enhance the observed flexibility of the catheter. The inner lubricious polymeric liner forms the inner lumen of the catheter.

The outer polymeric covering typically is constructed from a number of sections of polymers having different flexural moduli placed axially nose-to-tail. The helical coils may be attached to the inner lubricious layer by radio-opaque bands or coils. Those coils are desirably formed of a single, continuous, stainless steel or super-elastic alloy member (e.g., a ribbon or wire) wound from the distal end to the proximal end and then back typically to a point near (or, perhaps, at) the distal end of the catheter assembly. The pitch of the wound coils may be constant or varied as desired. Additional layers of wound coil may be applied as necessary or desirable to attain appropriate physical characteristics. For instance, it may be desirable to add a layer of helically wound coil proximally to provide greater "pushability." The catheter is configured so that at least the distal portion of the catheter has a critical bend diameter of no more than 3.0 mm, preferably no more than 2.5 mm, more preferably no more than 1.5 mm, and most preferably no more than 1.0 mm.

Figure 1:
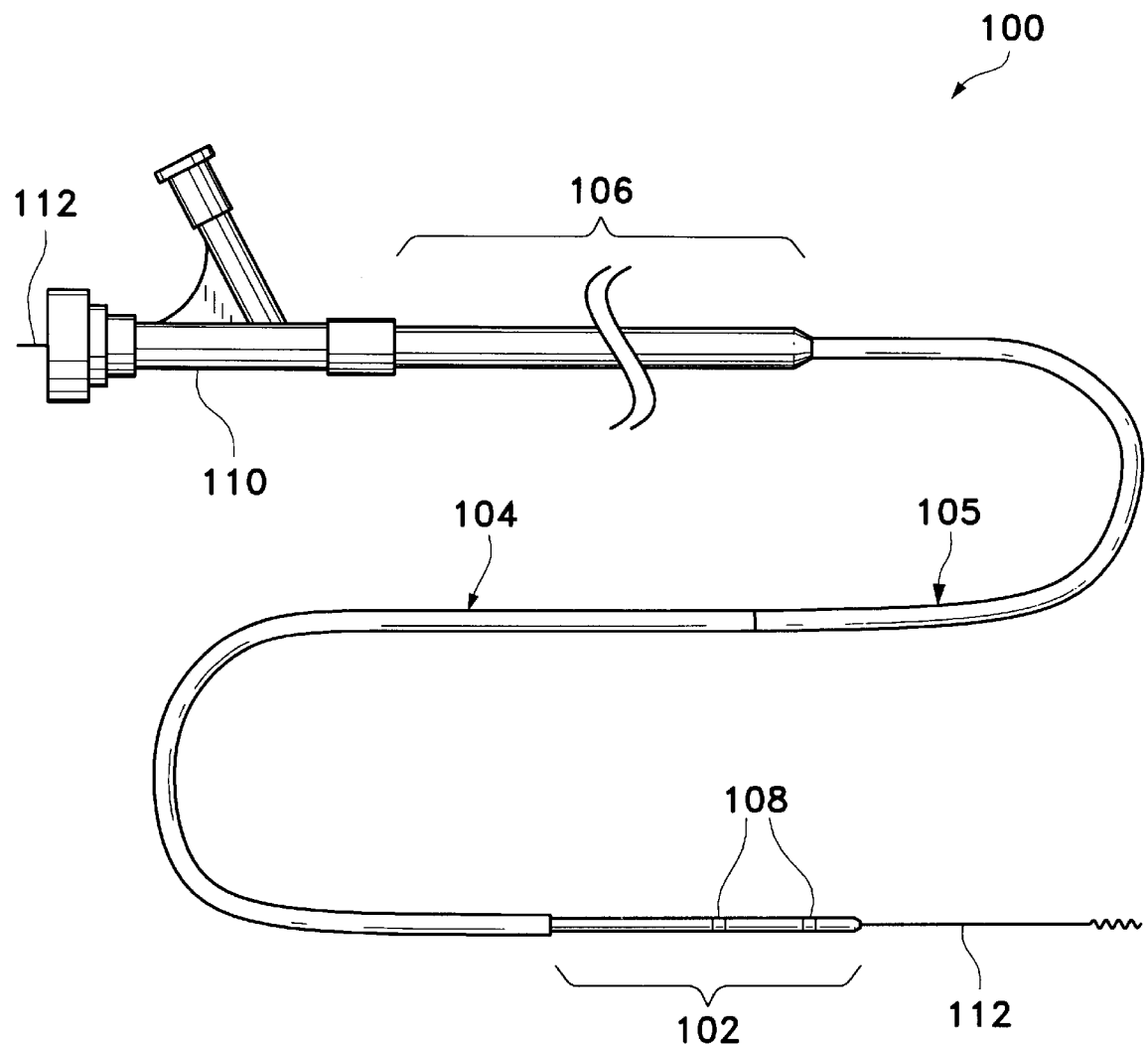
FIG. 1 shows, in side view, a typical multi-section catheter.

A typical neurovascular multi-section catheter (100) which may incorporate the concepts of this invention is shown in FIG. 1. The concepts of such a catheter are described in more detail in U.S. Pat. No. 4,739,768, to Engelson, (the entirety of which is incorporated by reference). The catheter design is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever narrower vascular areas. This smaller diameter requires a concomitant thinning of the wall section of the more distal portions of the catheter. This results in a further tradeoff in properties. The thinner distal section walls are able to attain even higher flexibility—a desirable trait because of the higher level of tortuousity in distal vasculature—but those thinner walls with their concomitent lower column strength are more prone to kinking or rippling when actively pushed along the guidewire or when vaso-occlusive devices are pushed through the catheter's lumen.

The configuration shown in FIG. 1 has a distal section (102) having significant flexibility, an intermediate section (104) which is typically less flexible, a second intermediate section (103) which is in turn less flexible than intermediate section (104), and a long proximal section (106) which in turn is least flexible. The distal section (102) is flexible and soft to allow deep penetration of the extraordinary convolutions of the neurological vasculature without trauma. Various known and often necessary accessories to the catheter assembly, e.g., one or more radiopaque bands (108) at the distal region to allow viewing of the position of the distal region under fluoroscopy and a luer assembly (110) for guidewire (112) and fluids access, are also shown in FIG. 1. The typical dimensions of this catheter are:

| | |
|---|---|
| Overall length: | 60–200 cm |
| Proximal Section (106): | 60–150 cm |
| Intermediate Section (105): | 5–50 cm |
| Intermediate Section (104): | 5–50 cm |
| Distal Section (102): | 2–30 cm |

Obviously, these dimensions are only guidelines, are not critical to this invention, and are selected as a function of the malady treated and its site within the body. However, as will be discussed below, use of the spiral wound members permits the walls of the catheter to be somewhat thinner with no diminution of performance, e.g., crush strength or flexibility, and, indeed, usually provides an improvement in performance, particularly in the area of kink-resistance.

FIGS. 2A–2F show a procedure for assembling the catheter shaft making up the catheter assembly of this insertion.

Figure 2A:
FIGS. 2A–2F schematically depict a method for producing a preferred variation of the inventive catheter.

FIG. 2A shows a simple mandrel (200) used as the support for producing the final catheter assembly. The mandrel (200) may be highly malleable, e.g., of copper or silver of the like, for ease of removal (by axial stretching of the mandrel and reduction of the mandrel's diameter) when the catheter shaft is completely assembled. Or, the mandrel (200) may be of a comparatively non-malleable material such as stainless steel if the mandrel (200) will slide easily from the catheter shaft at the end of the assembly procedure.

Figure 2B:

FIG. 2B shows the mandrel (200) with a polymeric tubing (202) placed thereon. This tubing is shown to be a single, continuous component in FIG. 2B and such is preferred, but the polymeric tubing (202) need not be continuous. Shorter sections may make up this portion where, e.g., different stiffness or parameters of slipperiness are needed.

Tubing member (202), which is also referred to as the "inner liner" elsewhere herein, is preferably formed of a lubricious polymer. Suitable polymers include many of the fluorocarbons sold as Teflon although polytetrafluoroethylene (PTFE or TFE), such as is sold by Zeus Polymers, Inc., is preferred.

In our experience, these small PTFE polymeric tubes are available in two important and thin-wall variations: shrink-wrappable and non-shrink-wrappable. For instance, the desired shrink-wrappable tubing is available with, e.g., a wall thickness of 0.7 mils or less. After shrinking onto the forming core mandrel, the wall thickness increases to perhaps 1.0 mils. The PTFE tubing which is not to be "heat-shrunk" onto the mandrel is often a better choice for this service because, as discussed below, it may be axially stretched to form an inner layer which is much thinner, e.g., a 1.25 mil wall polymeric tube will form a 0.7 mil inner lubricious layer upon axial stretching.

Other suitable lubricious polymers include polypropylene, the Nylons, FEP, polypropylene, and the like.

As noted above, it is sometimes desirable when using fluorocarbon polymers as the constituent of the inner liner (202), that the exterior of the tubing be etched prior to further assembly to provide a suitable chemical or physical bond with any additional outer polymeric coverings. Such etchants are commercially available.

Additionally, the inner liner (202) may be axially stretched after placement upon the mandrel for any of a variety of purposes, e.g., axially orienting or aligning the polymeric molecules, "straightening" the inner and outer tubular surface, thinning the tubing wall, etc. It is also desirable at this point to place a tubular layer acting as a filler layer and, perhaps as an adhering layer exterior to the inner polymeric layer (202). This layer is not shown in the drawing but is discussed in more detail below.

Figure 2C:
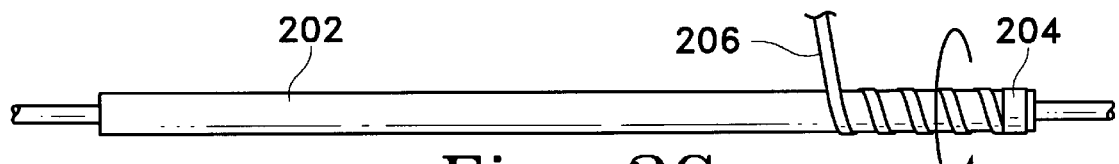

FIG. 2C shows an optional step in the production of the catheter body in which a radio-opaque band or coil (204) is placed over the ribbon (206) to hold that ribbon (206) in place and the whole subassembly is rotated to wind the ribbon (206) onto the inner tubing member or liner (202).

Although not necessary, it is within the scope of this invention to include an adhesive between the inner polymeric liner (202) and the ribbon (206). Thermoplastic elastomers (such as Hytrel) and ethyl vinyl acetate (EVA) are choices for such an adhesive.

Figure 2D:
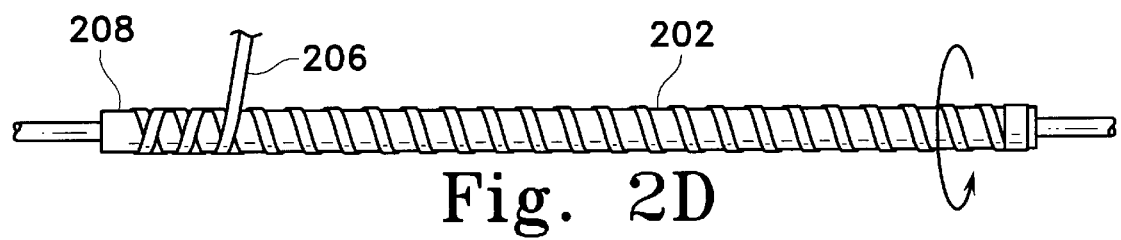

FIG. 2D shows the winding of the ribbon (206) after it has passed to the proximal end (208) of the inner polymeric liner (202) and is being wound back towards the distal end of the subassembly. It should be noted that the pitch of the windings both as the ribbon is passed proximally and as it is returned distally may vary to provide optimum flexibility and kink-resistance.

For instance, the pitch may be widened to provide additional torqueability in the proximal end of the assembly. Widening the pitch decreases the pushability of the section. Similarly, in the distal end of the catheter where torqueability is less a concern and kink resistance and flexibility are, the spacing between turns may be varied to optimize those physical parameters. However, for a specific wire or wire size and desired kink-free turn diameter, there is a pitch which optimizes the flexibility of the catheter section containing it—decreasing the pitch from the optimum causes the coil to bind against itself and become less flexible when the section is bent and significantly increasing the pitch from the optimum causes the coil's lateral flexibility to begin to approach the inherent lateral flexibility of the constituent wire or ribbon. Care must be taken to select a spacing which does not cause binding between turns during normal (and abnormal) bending operations. We have found a turn spacing that optimizes the summary parameter of trackability for these neurovascular catheters and will discuss such optimum spacing in more detail below.

The spiral wound ribbon (206) shown in FIGS. 2A–2F may be of a variety of different materials. Although metallic ribbons are preferred because of their strength-to-weight ratios, fibrous materials (both synthetic and natural) may also be used. Desirable, because of cost, strength, and ready availability are stainless steels (SS308, SS304, SS318, etc.) and tungsten alloys. The Young's modulus of a stainless steel such as the preferred 304SS (vacuum refined) is perhaps three times that of a typical nickle/titanium super-elastic alloy. Consequently, a ribbon of stainless steel may be much smaller than a comparable super-elastic alloy ribbon with comparable strength. In certain applications, particularly smaller diameter catheter sections, more malleable metals and alloys, e.g., gold, platinum, palladium, rhodium, iridium, etc. may be used. A platinum alloy with a few percent of tungsten is desirable because of its radio-opacity and ease of working. A platinum alloy with a few percent of iridium is preferred because bands fashioned from such an alloy may be quite thin and yet have very high radio-opacity.

The class of alloys known as super-elastic alloys is also a desirable selection. Preferred super-elastic alloys include the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. These alloys are commercially available in the small ribbons required by the invention described here, but for very high performance catheters are excellent choices. Other super-elastic or high performance alloys suitable for this use include MP35N, SYNTACOBEN, or ELGELOY and the like.

Metallic ribbons (206) that are suitable for use in this invention are desirably between 0.25 mil and 1.5 mil (preferably 0.25–0.75 mils and more preferably 0.35–0.60 mils) in thickness and 1.0 mil to 8.0 mils (preferably less than 3.0 mils and most preferably 1.0–3.0 mils) in width, particularly when stainless steels are used. By the term "ribbon", we intend to include elongated shapes, the cross-section of which are not square or round and may typically be rectangular, oval or semi-oval. They should have a cross sectional aspect ratio of no more than 0.5 (thickness/width). In any event, for stainless steels, the thickness and width may be somewhat finer, e.g., down to 0.25 mil and 1.0 mil, respectively.

Suitable non-metallic ribbons include high performance materials such as those made of polyaramids (e.g., KEVLAR), liquid crystal polymers (LCP's), and carbon fibers although the modulus of elasticity is perhaps ⅓ to ⅙ that of the stainless steels listed above.

Suitable for this variation and others described herein is the use of wire in place of the preferred ribbon. The wires, variously of round, oval, square or other similar cross-section, have an aspect ratio of 0.5 or more (thickness/width as placed on the catheter assembly) and preferably near 1.0.

Figure 2E:
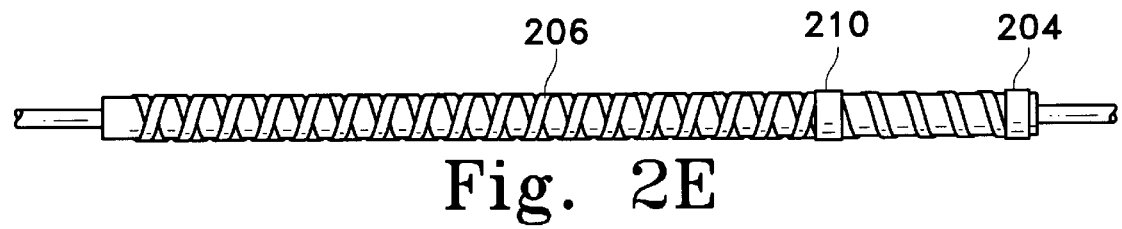

FIG. 2E shows the completed wrapping or winding of the helically wound coil (296) and its final attachment to the subassembly via a radio-opaque member (206). Radio-opaque members (204, 210) are generally solid bands, bands with axial cuts, or coils of a malleable radio-opaque metal as discussed above. This variation is the one we call the "continuous wind" variation since ribbon (206) is a continuous band.

As was the case above, it is within the scope of this invention to place an adhesive on the exterior of the assembly at this point to assist in providing adherence of the ribbon (206) and inner liner (202) to the outer polymeric coverings (212, 214, 216, and 218) discussed below. The use of adhesives in this step or in that mentioned above depend principally upon the choice of materials in those outer polymeric coverings.

Figure 2F:
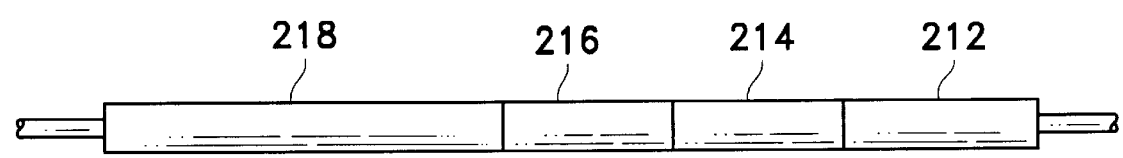

FIG. 2F shows the assembly with a number of outer polymeric tubing sections (212, 214, 216, 218) as placed on the exterior with the ribbon (206). The distal-most section (212) is typically the softest and most flexible. As may be apparent from a comparison of FIGS. 2E and 2F, section (212) is typically placed only over the distal portion of the assembly in which the ribbon (206) is wound in a single layer. Desirably, the proximal radio-opaque marker (210) and the distal radio-opaque marker (204) fluoroscopically bracket the distal section of the assembly.

Sections (214, 216, and 218) are axially contiguous tubing members and are generally harder and less flexible, e.g., as measured by durometer and flexural modulus, as the proximal end is approached. We have found that three sections of increasing flexibility is generally adequate and consequently sections (214, 216) of the outer polymeric covering may be combined. Four such sections are preferred.

A wide variety of polymers are acceptable as materials for the outer polymeric covering sections (212, 214, 216, 218). Shrink wrap polyethylene, e.g., polyethylene tubing containing a sufficient amount of a cross-linking agent such as EVA, which has been stretched and irradiated, is suitable.

We prefer PEBAX (a proprietary polyether-polyamide material) although various blends such as CARBOTHANE, TECOFLEX, and TECOTHANE, often containing polyurethane, are also suitable. Although these materials are not shrink-wrappable polymers per se, they may be accurately placed on the catheter shaft assembly in the following manner. The various sections of tubing are cut to length and placed over the wrapped catheter shaft subassembly shown in FIG. 2E. A shrink wrappable layer of polyethylene tubing is then placed over the tubing and heated so to shrink-wrap the polyethylene and pull the tubing into intimate contact with the reinforcing member (206) winding and perhaps with the inner liner (202). Some thought must be had for selection of polymer composition having appropriate $T_g$'s with relation to the shrink-wrap temperature of the polyethylene layer. The polyethylene layer may be left in place or, desirably, be stripped away exposing the outer polymer covering.

Polymers suitable for this service include known materials such as polyethylene, polyvinylchloride (PVC), ethylvinylacetate (EVA), polyethylene terephthalate (PET), and their mixtures and copolymers. One very useful class of polymers are the thermoplastic elastomers, particularly polyesters. Typical of this class is HYTREL. This is not to exclude the use of other polymers, depending on the section of the catheter. For instance, the tubing may be of any of a variety of polymers, variously stiff or flexible. For instance, for section (218), the polymer may be a polyimide, polyamides such as the Nylons, high density polyethylene (HDPE), polypropylene, polyvinylchloride, various fluoropolymers (for instance: PTFE, FEP, vinylidene fluoride, their mixtures, alloys, copolymers, block copolymers, etc.), polysulfones or the like. Blends, alloys, mixtures, copolymers, block copolymers, of these materials are also suitable, if desired.

If a more flexible section is required, the outer tubing member may be a polyurethane, low density polyethylene (LDPE), polyvinylchloride, THV, etc. and other polymers of suitable softness or modulus of elasticity. The wall thickness of the outer tubing member (206) may be as thin as 0.5 mil and as thick as 10 mil, depending upon catheter usage, portion of the catheter, polymer choice, and the style of catheter.

Typically, the wall thickness of the inner liner (202) will be between 0.5 and 3.0 mils. This dimension is obviously only a range and each catheter variation must be carefully designed for the specific purpose to which it is placed.

It should also be noted that each of the polymers discussed herein may be used in conjunction with radiopaque material or fillers such as barium sulfate, bismuth trioxide, bismuth carbonate, powdered tungsten, powdered tantalum, or the like so that the location of the various pieces of tubing may be radiographically visualized within the vessel.

Returning to FIG. 2F, mandrel (200) may be removed and assembly of the catheter shaft is complete. Of course, as shown below, the addition of a proximal fluid handling member, e.g., with a Luer-lock, is necessary and subsequent treatment with a material to provide enhanced lubricity, perhaps by bonding with a hydrophilic polymer coating, is desirable.

Although the production of a catheter having a continuous length of a wire or ribbon in two layers is highly desirable, this invention includes catheters having multiple layers of wire or ribbon wrapped onto the catheter core assembly variously as a single length, by changing the direction of the wrapping as a specific layer is produced, or by using multiple lengths of wire or ribbon. Additionally, as noted above, the invention includes the use of multiple coils wrapped in the same or in opposite directions about the catheter assembly's core. The pitch of any or all of the layers may be constant in a single layer or may vary as desired, e.g., by step, continuously, or to suit a specific flexibility requirement. The pitch of each layer may be the same as or different than the pitch of the other layers.

An additional variation of this invention is the use of double coils only in the more distal segments of the inventive device leaving at least the more, or most, segment or segments with a structure reinforced by tubing, braiding, or a single coil or the like.

FIGS. 3A through 3D show schematically the production of a catheter assembly having a dual coil layer.

Figure 3A:
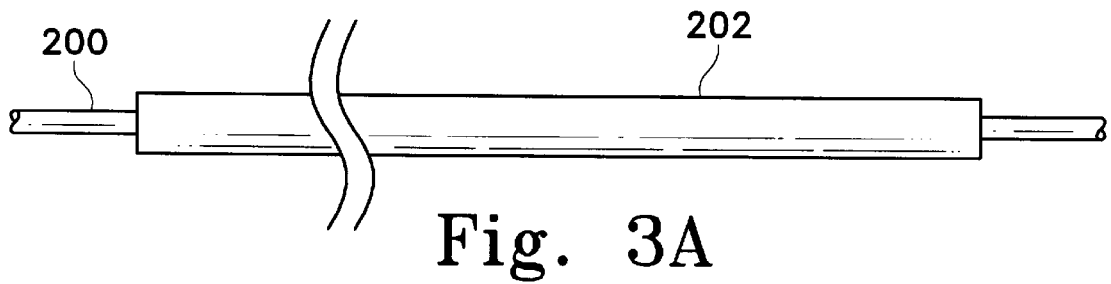
FIGS. 3A–3D show a method for producing a variation of the inventive catheter.

FIG. 3A shows the same core assembly as was shown in FIG. 2B above: Mandrel (200) and interlubricious layer (202).

Figure 3B:
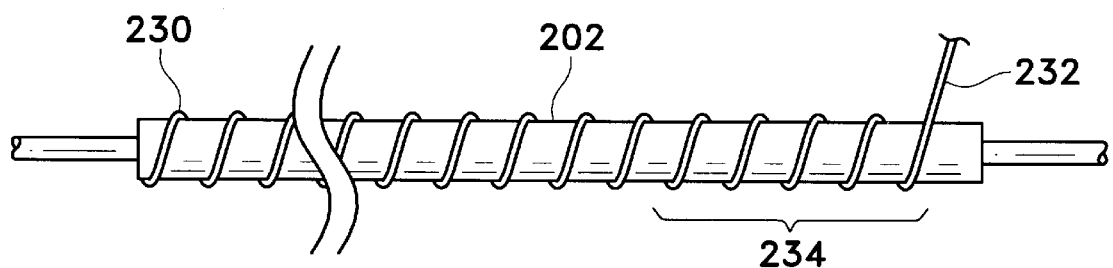

FIG. 3B shows the step of wrapping a first layer (230 of wire onto the inner layer (202). The wire (232) is shown in the distal region of the assembly to have a different pitch (234) than in the more proximal regions.

Figure 3C:
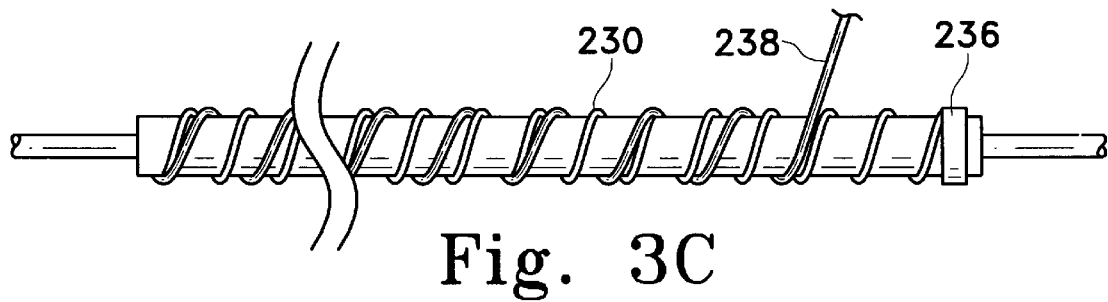

In FIG. 3C, a radio-opaque band (236) has been placed distally on the inner wire wrapping (230). Also shown in FIG. 3C is a second wire wrapping (238) which has a different pitch than that found in the first layer (230).

As has been noted above, the second layer (238) may have the same pitch as first layer (230). It may have different pitch than the first layer (230) or each of them may have variable pitch as desired. As noted above, the wire used in this variation and in any of the others noted herein may be wound in cross-section, oval, or square. Concepts discussed in relation to this variation of the invention are applicable both to variations using wire and to variations using ribbon materials as the stiffeners.

Figure 3D:
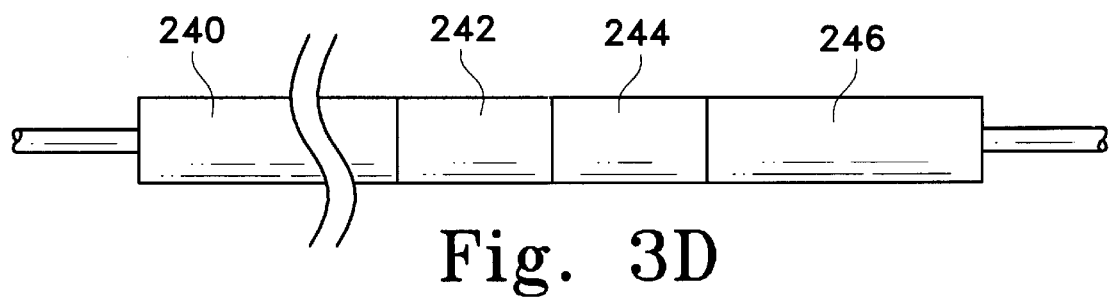

FIG. 3D shows the core assembly with placement of four regions of polymer outer covering (240, 242, 244, and 246). It is within the scope of this invention that polymer segment (240), located at the catheter assembly more proximal and, as the length of 80 to 100 centimeters. A desirable material for this segment may be any of the materials described above but most preferably is one having a durometer value between 65D and 80D, most preferably 72D. The adjacent section (242) most desirably has a length of 5 to 20 cm and is of a polymer material having a durometer value between 55D and 70D, most preferably 63D. Segment (244) similarly, and preferably, has a length between 5 and 20 centimeters and is preferably of softer material than those more proximal. It may have a durometer value of 50D to 60D, most preferably 55D. Finally, segment (246) is located at the most distal end of the catheter and is typically of a length between 2 and 20 centimeters and is most flexible, preferably of a material having a durometer value between 20D and 40D, most preferably 25D. We find the preferred material to be the polyether-polyamid material known as PEBAX, discussed above.

Figure 4:
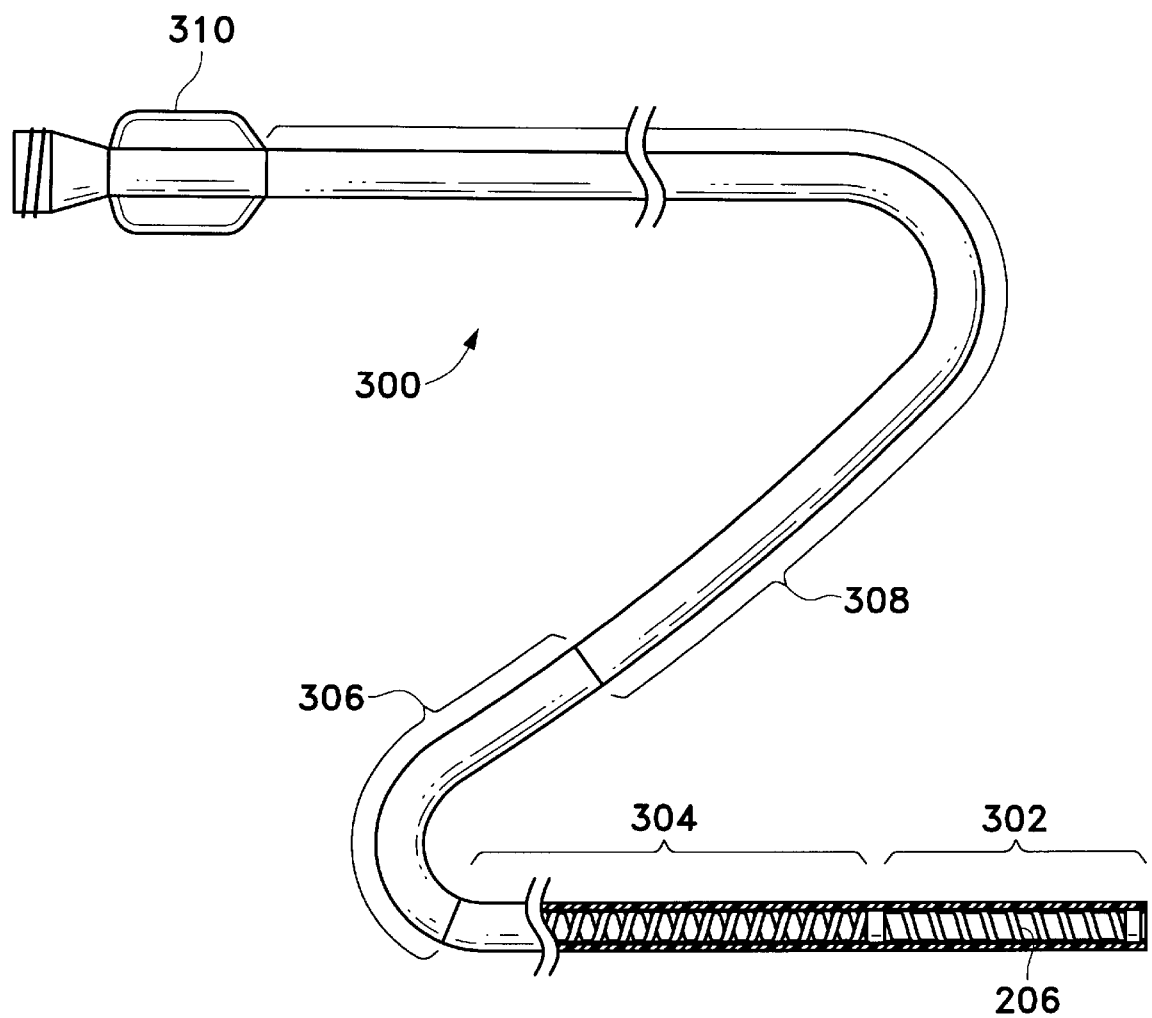
FIG. 4 shows, in partial cross-section, a variation of the invention made using the procedure of FIGS. 2A–2F.

FIG. 4 shows the variation of the inventive catheter (300) as finally assembled using the procedure shown in FIGS. 2A–2E. The numerous sections (302, 304, 306, and 308) of increasing stiffness proximally may also be seen. The connector portion (310), located proximally, allows connection with fluid delivery means or guidewire handling devices.

The single layer of ribbon (206) is shown in the cutaway of distal-most section (302). The multiple layers of ribbon are shown in the cutaway of the next more proximal section (304).

Figure 5:
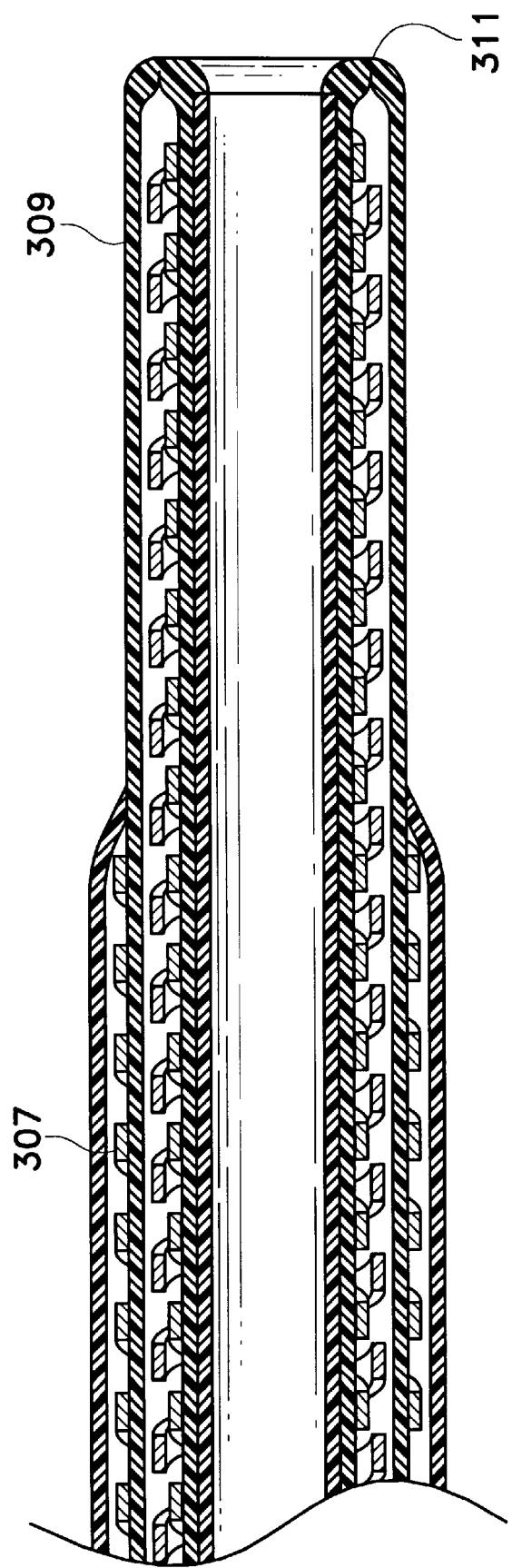
FIG. 5 shows a variation of the inventive catheter with an additional helically wound coil located proximally.

FIG. 5 shows a variation of the inventive catheter in which a third layer of ribbon (307) has been placed proximally on the catheter assembly to enhance the "pushability" of the catheter assembly. Also shown is the use of a dual layer of ribbon coils to a point near the distal tip (309). A small "nose" or distal tip (311) of polymer remains distal of the distal-most extension of the coil windings. Use of layers of coil in excess of the preferred dual layer distal-to-proximal layers is a feature independent of the presence or absence of other features, e.g., the distal nose tip section (311), shown in this Figure or in others.

Figure 6A:
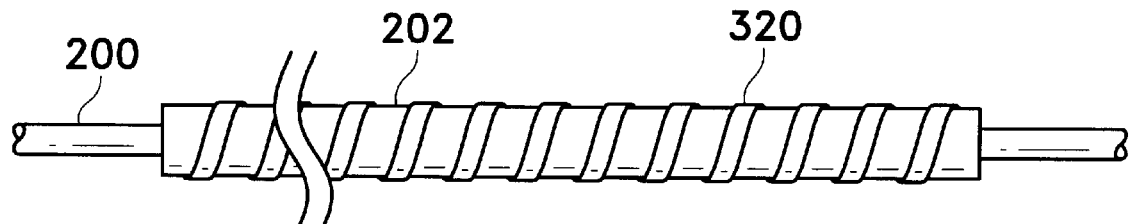
FIGS. 6A–6E show a method for producing a variation of the inventive catheter having a stiffer proximal section.
Figure 6B:
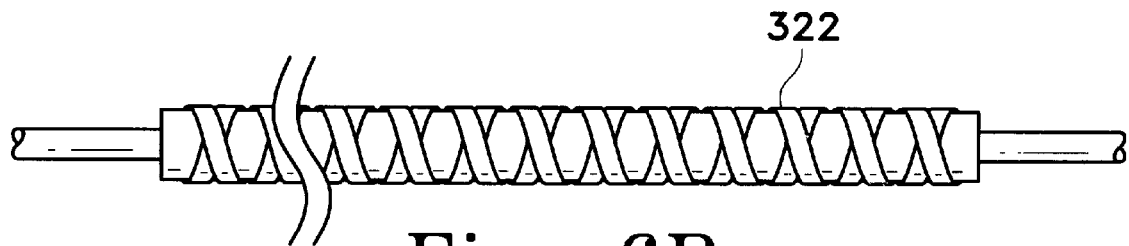

FIGS. 6A through 6B show, in schematic fashion, the production of catheter assembly having four layers of coil reinforcement. This variation uses counter-wound layers of ribbon stiffening material. It may, instead, use wire which is co-wound, i.e., wound in the same direction or a mixture of ribbon and wire. This variation shown in FIGS. 6A through 6E is for the specific purpose of providing significantly higher torque ability and push ability due to reinforcement of the more distal portion of the catheter assembly.

FIG. 6A simply shows a mandrel (200) and an inner lubricious layer (202) and a first layer of ribbon (320).

FIG. 6B shows a counterwound ribbon (322) extending the length of the catheter.

Figure 6C:
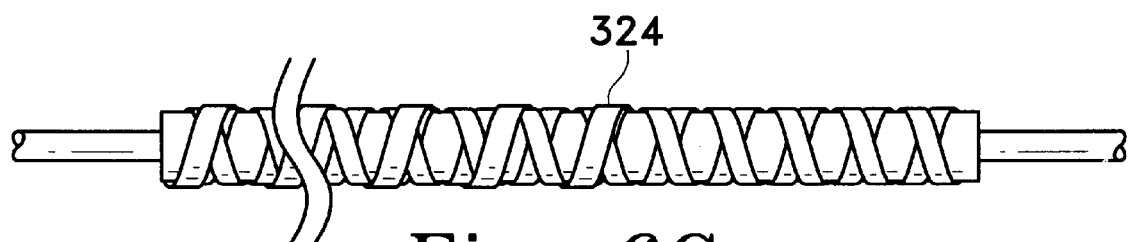
Figure 6D:
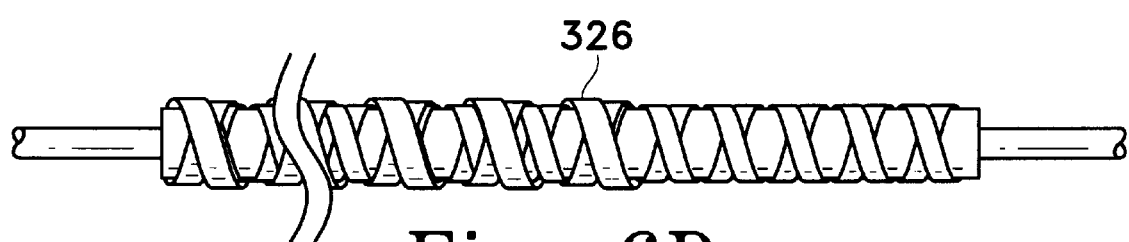

FIG. 6C shows a third level of counter-wound ribbon on the more proximal portion of the catheter assembly. For instance, ribbon (324) might extend for all but the most distal 50 centimeters of the inventive device. FIG. 6C shows the final layer of counter-wound ribbon (326).

Figure 6E:
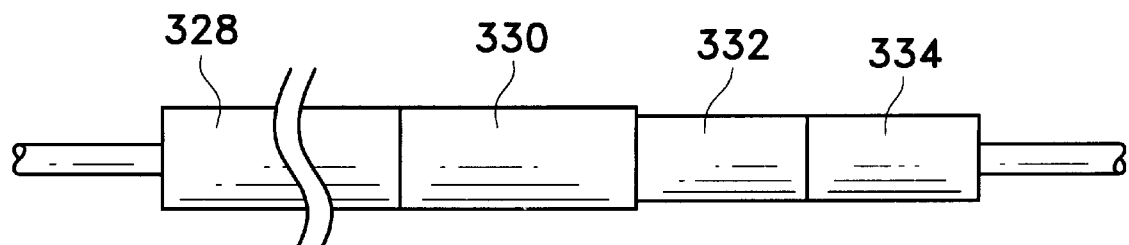

Finally, FIG. 6E shows the introduction of several polymeric layers (328, 330, 332, and 334) onto the subassembly produced above. Again, a catheter produced in this way has superior pushability and column stiffness due to the enhanced stiffness from the more proximal ribbons. We have found that use of thinner ribbons or smaller diameter wires in each of these layers produces an exceptional catheter with modest profile and superior kink resistance and flexibility.

Figure 7:
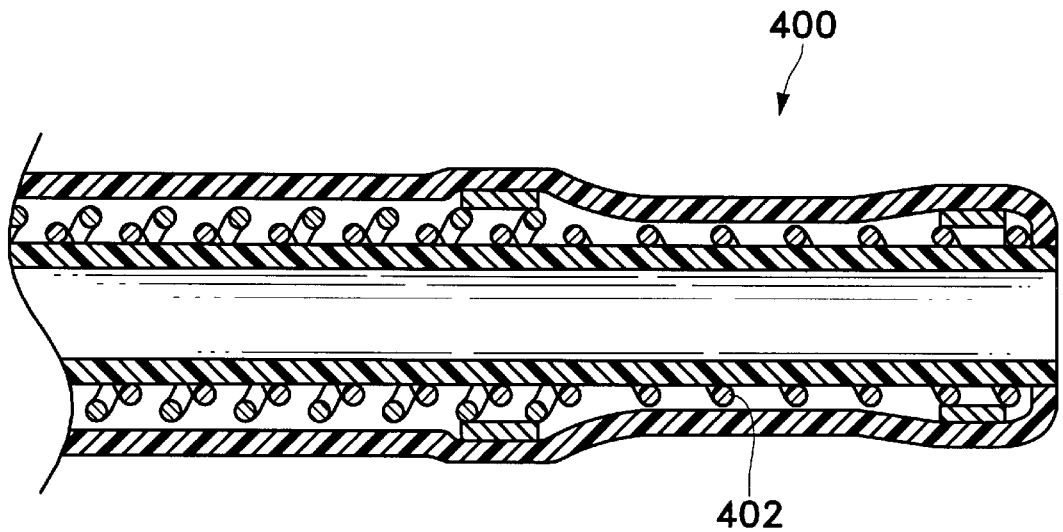
FIGS. 7 and 8 show, in cross-section, variations of distal tips of the inventive catheter.

FIG. 7 shows a cross-section of the distal end (400) of the variation shown in FIG. 3 but, with the exception that the helical coil (402), is formed of a wire rather than a ribbon. By "wire" we mean a member having a round, square, oval, or similar cross-section with an aspect ratio of 0.5 (thickness/width) or less.

Figure 8:
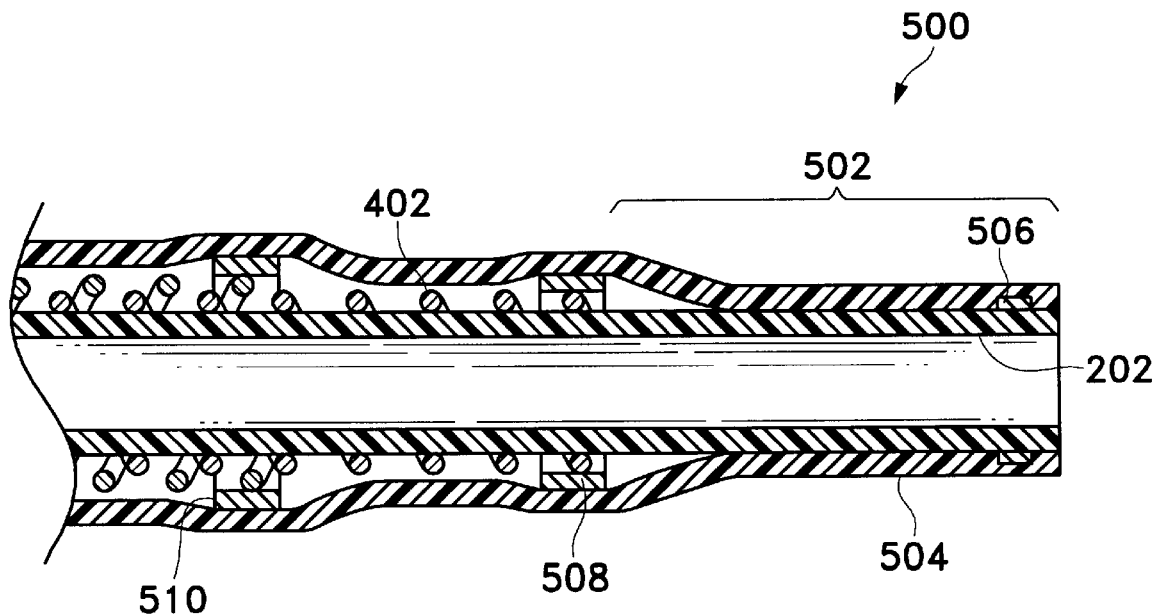

FIG. 8 shows a cross-section of the distal end (500) of a variation in which the helically wound coil (402) does not extend to the distal tip. In this variation, the most distal section (502) is comprised of an outer layer (504) and an inner polymeric liner ((202). Multiple radio-opaque markers (506, 508, 510) are shown. Markers (508, 510) are used to attach the helical coil (402) ends to the inner liner (202) and depict ends of the various flexibility regions.

Figure 9:
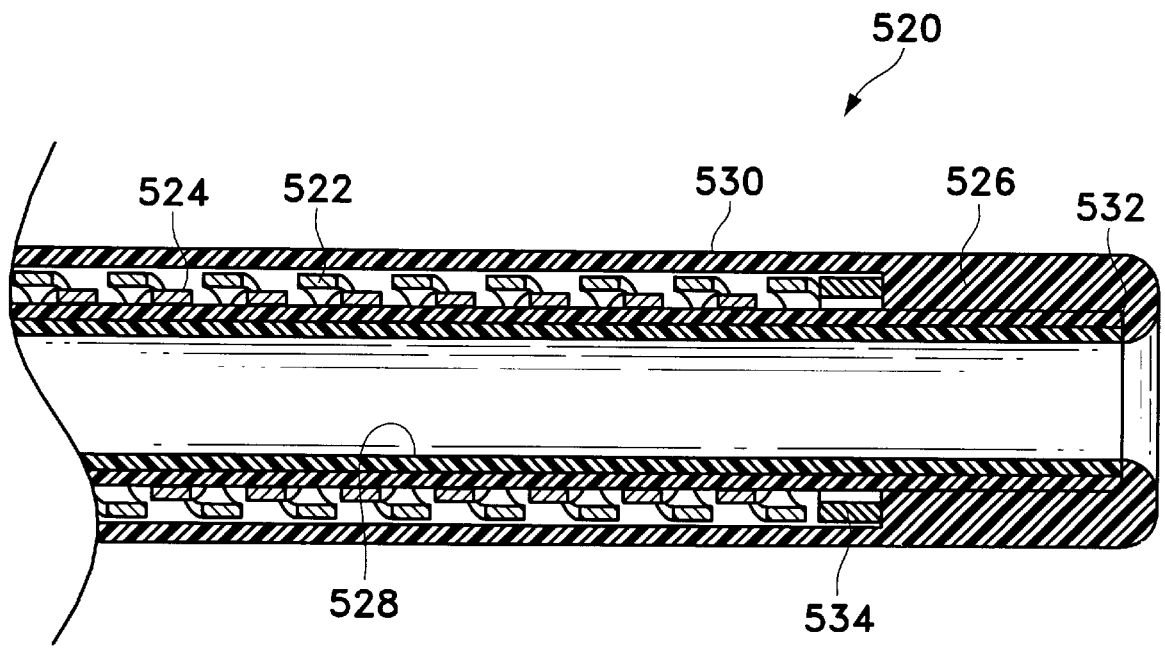
FIG. 9 shows, in cross-section, a highly preferred variation of the distal tip of the inventive catheter.

FIG. 9 shows a distal portion (520) of the inventive catheter in which both helically wound coils (522, 524) extend distally to a tip or bumper (526). Distal tip (526) is relatively short, typically having a length of no more than about 10–15 times the diameter of the device. In general, it is made up of the inner liner (528) and a mixture of the outer layer (530) and the filler layer (532) between the inner coil (524) and the lubricious liner (528). A single radio-opaque marker (534) is shown. For the purposes of describing this invention, a short bumper tip (526) is considered to have a negligible effect on the operation of the catheter assembly (other than to protect the intima of the arteries from damage by the coil members). When we note that a coil extends to the distal end of the catheter, we intend such a statement nevertheless to include the presence of such a bumper tip (526). It is specifically noted that, however, the short distal tip (526) shown in FIG. 9 is not the same structural feature as is the comparatively lengthy most-distal section (502) in FIG. 5 which, in practice, may be 2.5 cm. or longer. Indeed, the bumper tip (526) may be used in conjunction with most-distal section (502).

Figure 10:
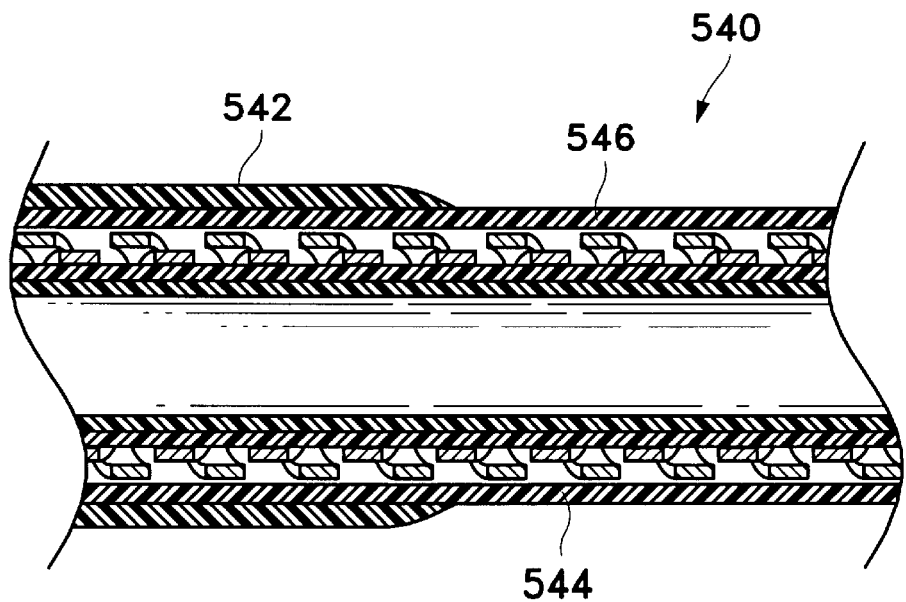
FIG. 10 shows, in cross-section, a desirable intermediate section suitable for use in the inventive catheter.

FIG. 10 depicts a variation (540) of a midsection of a highly desirable variation of this invention. It merely depicts the use of an additional exterior layer (542) on a midsection (544) which may be similar to a portion of the catheter shafts depicted in, e.g., FIG. 9 above. Such an outer layer may be of a wide variety of material chosen either to enhance the lubricity of the overall catheter assembly or to provide additional stiffness to that section. It is desirable to use materials such as PEBAX (discussed elsewhere) which are compatible with the layer just interior to layer (542). Adhesive materials may be placed between respective layers if so desired or if necessary.

Figure 11:
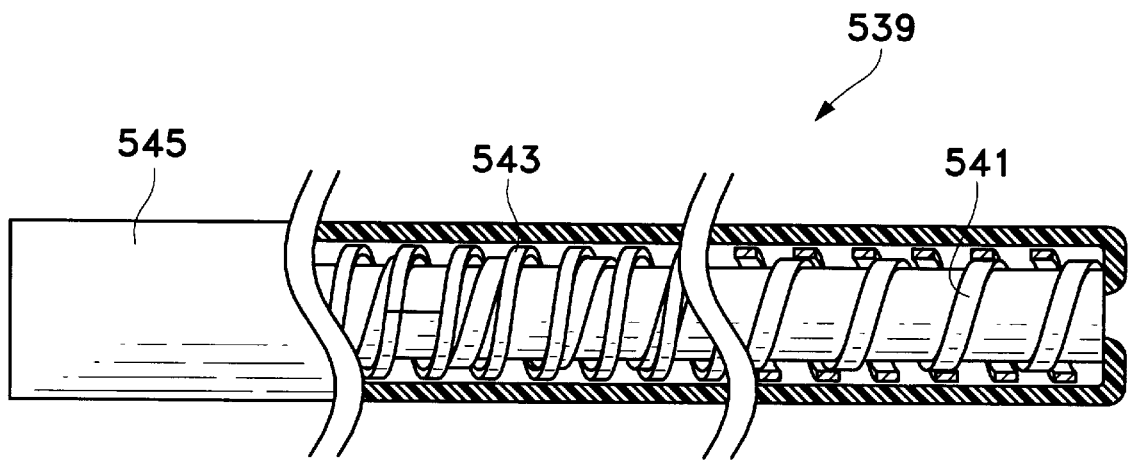
FIGS. 11 and 12 show, in partial cutaway, variations of the distal end of the inventive catheter.
Figure 12:
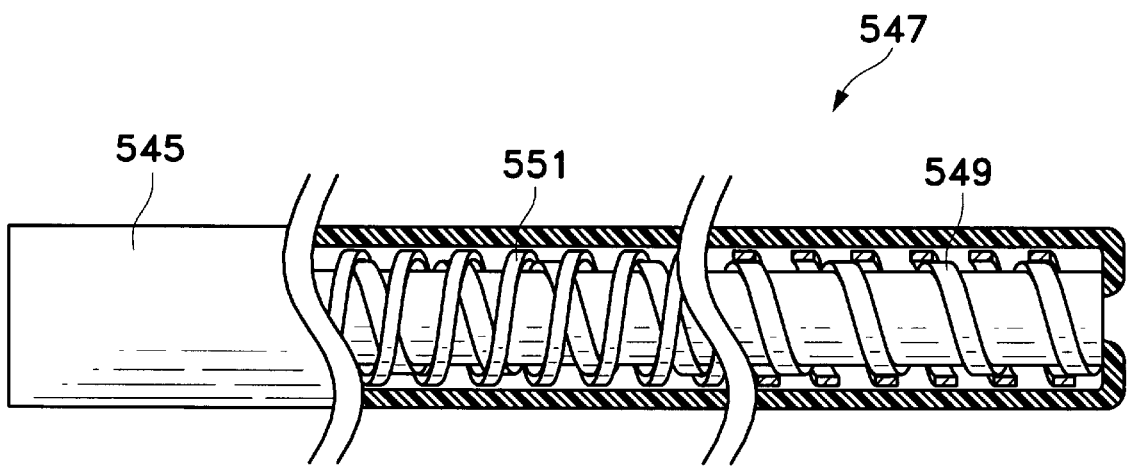

FIGS. 11 and 12 depict in schematic fashion the use of dual coil reinforcing assemblies only in the more distal regions of catheter assembly. In FIG. 11, catheter assembly of (539) utilizes inner coil (541) and an outer coil (543) in the distal portion of catheter assembly (539). In this instance, inner ribbon coil (541) has a wider ribbon than the more square wire (543) found in the outer layer. The pitches of the two layers (541 and 543) are different because of the size of the materials involved but the angles of the two coils (541 and 543) are quite similar as measured from the axis of the catheter.

The more proximal portion of the catheter (545) may be of any appropriate design for the medical service involved. For instance, for neurovascular service, the more proximal portion may be a simple multi-layered polymeric shaft. This might take the form of polypropylene or polyimide layer, perhaps with the extensive inner lubricioius layer discussed above at length with regard to other variations. An outer shrink wrap covering may also be included. It is within the purview of this invention that a single layer of polymeric material, if of the appropriate mechanical capabilities, be used. Metallic hypotubes of stainless steel or super-elastic alloys may also be employed. It is within the purview of this invention that the more distal portion (545) be of a single coil or multiple coil construction or may be of braided construction.

FIG. 12 shows a similar variation (547), having an inner ribbon coil (549) and an outer ribbon coil layer (551). Inner layer (549) is of counter-wound to outer layer (551). Otherwise, the variation of (547) is of similar in other respects to the variation described with respect to FIG. 11.

Figure 13A:
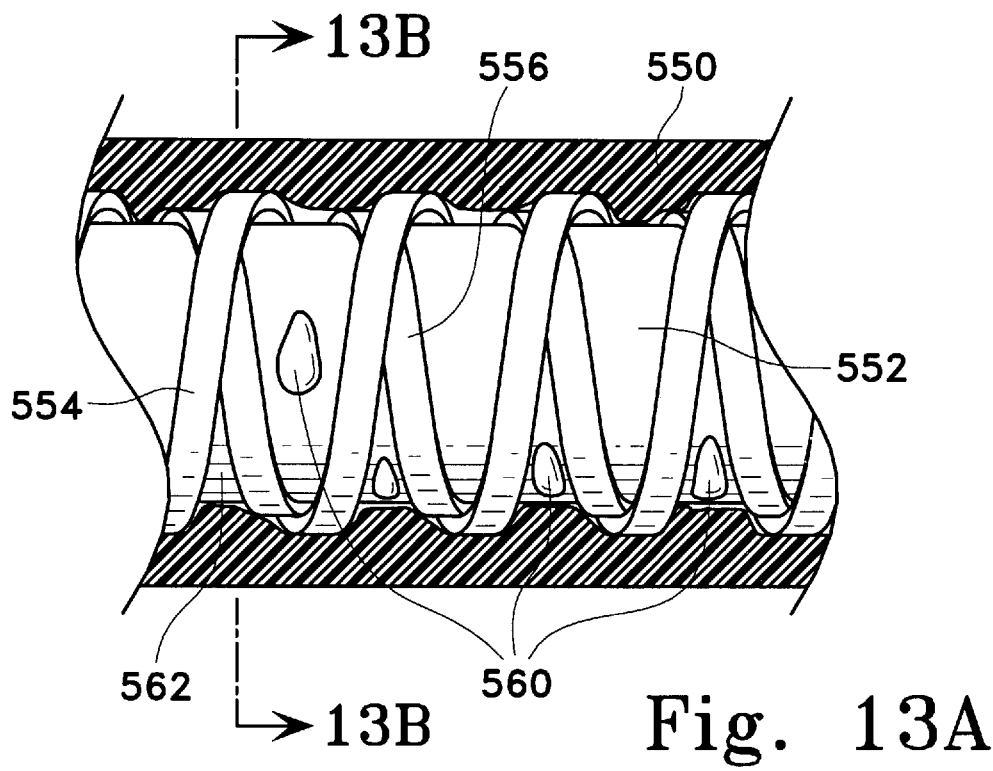
FIG. 13A depicts in partial cross-section the approximate configuration of the polymeric material making up the outer covering.
Figure 13B:
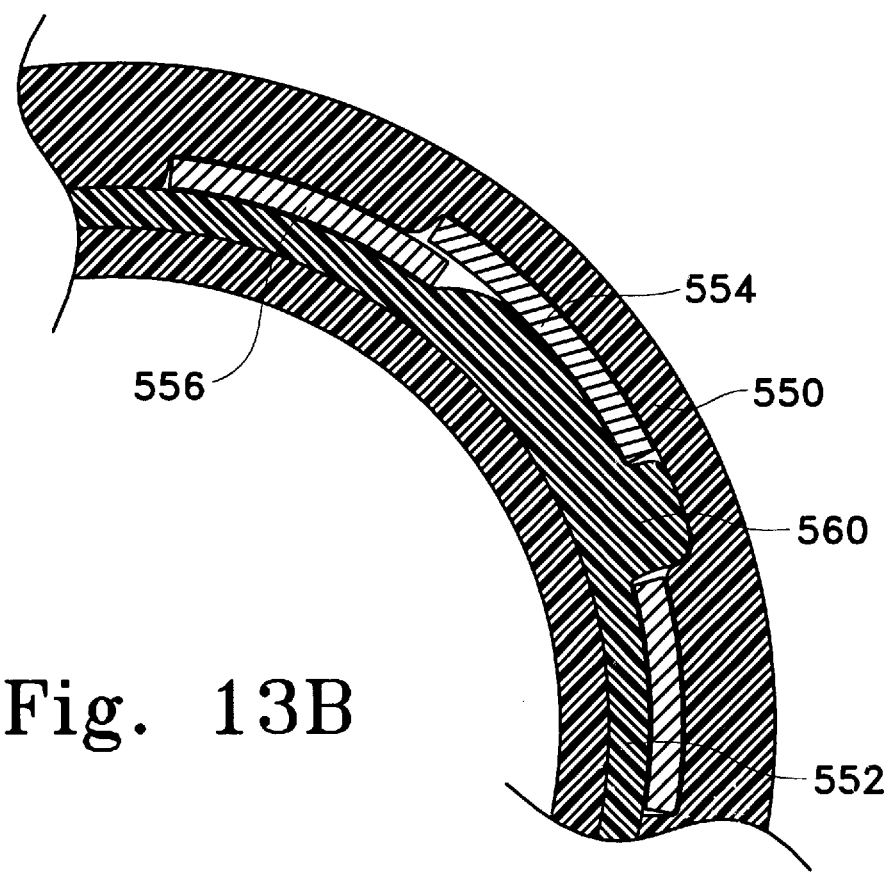
FIG. 13B is a cross-section looking axially of the FIG. 13A variation.

FIGS. 13A and 13B show respectively in side cross-section and end cross-section what is believed to be a significant mechanism of the instant invention.

FIG. 13A shows a partial cross-section having an outer layer (550) and an inner layer (552). The preferred crossing ribbons (554) on the exterior and (556) on the interior are also shown. Also are shown various islands (560) which are artifacts created as a result of squeezing the outer layer (550) onto the inner layer (552) with sufficient heat. Although it is believed that these islands are separated by open regions (562), it is believed that this combination of pillars (560) and open regions (562) provide the catheter assembly itself with a great deal of suppleness. It is further believed that when one of the coils (556, 554) are removed, the resulting polymeric material forms a sort of polymeric spring which is bonded directly between inner layer (552) and outer layer (550). This continuous region in a single ribbon catheter appears to provide significant stiffness to the catheter assembly typically equal to that found in the preferred dual counter-wound ribbon assembly shown in FIGS. 13A and 13B.

FIG. 13B shows, with greater clarity, island (560) between outer layer (550) and inner layer (552). Outer ribbon (554) and inner ribbon (556) may also be seen in FIG. 13B.

Typical catheters made using this invention are in the 1.5 French to 5 French range. The typical inner diameter of such catheters is then 10 mils to 42 mils. However, microcatheters may be made using these concepts having outside diameters of 18 mils to 36 mils. The inner diameter of those catheters was 11 mils to 30 mils. The invention is not limited to such sizes, however.

As was noted above, the most distal portion of the distal section of this catheter (and preferably other sections as well) have a critical bend diameter of no more than 3.0 mm, preferably no more than 2.5 mm, more preferably no more than 1.5 mm, and most preferably no more than 1.0 mm. To some extent, the critical bend diameter is also dependent upon the diameter of the catheter section and its components. For instance, we have made 3 French catheter section of the type shown in FIG. 2 (of stainless steel ribbon) with critical bend diameters less than 2.5 mm. Similarly, we have made catheter sections such as the inner catheter (275) shown in FIG. 4 with an outer diameter of 0.018" (of platinum-tungsten alloy ribbon) with bend diameters less than 1.0 mm.

FIGS. 14A to 14G show a highly desirable procedure for placement of a vaso-occlusive band or marker someplace within the confines of the catheter made according to this invention or to other catheters requiring such a band.

Figure 14A:
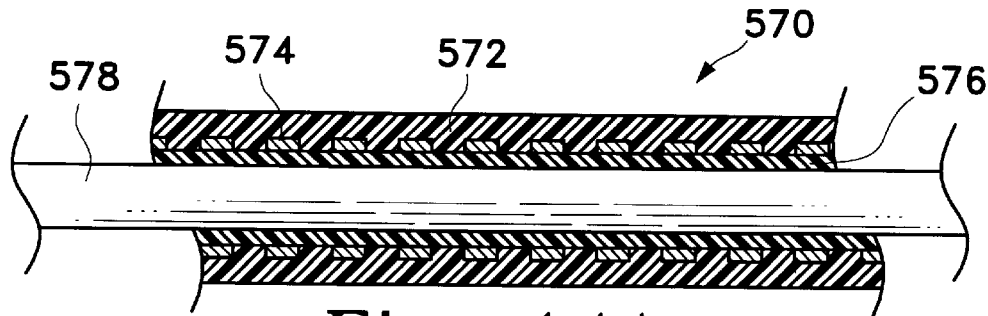
FIGS. 14A to 14G show a highly desirable method for introducing a radio-opaque member into the inventive catheter.

FIG. 14A shows a catheter section (570) which may have been made according to the invention as described above. This catheter section comprises an outer layer (572), a coil or braid member (574), and an inner layer (576). Outer layer (572) must be thermoplastic to be useful in the procedure described below. Inner layer (576) is typically lubricious and has a $T_g$ which is higher than the flow temperature material making up outer layer (572). Also shown in the partial cross-section of FIG. 10A is a mandrel (578) which simply serves to provide shape to the catheter section (570) during the thermal processing steps described below.

Figure 14B:
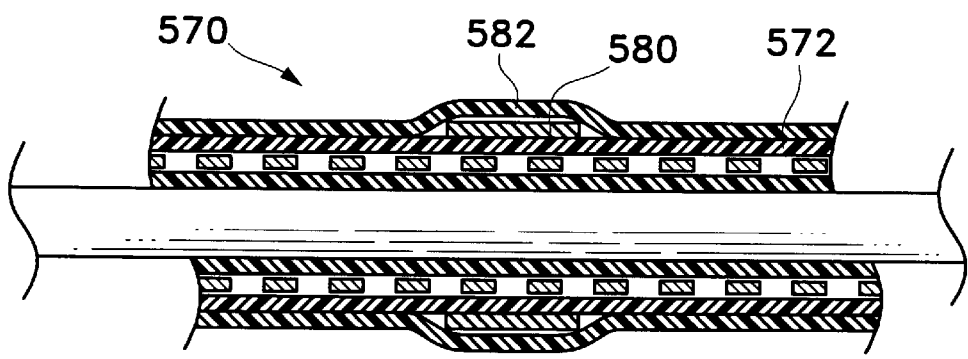

In FIG. 14B, an expanded polymeric ring (580) is situated over outer layer (572) at the approximate axial position where the radio-opaque band is later to be placed. The polymeric band (580) is one which upon application of heat will pull down to a smaller diameter via "shrink-wrap" phenomenon. Furthermore, an outer shrink-wrap tubular member (582) is placed over the catheter section (570). The materials of choice for variously outer layer (572), polymeric band (580), and outer tubing member (582) must be chosen with the following criteria in mind. The temperature at which outer shrink-wrap tubing (582) and polymeric band (580) undertake their shrinkage must be one at which the material making up outer layer (572) will flow. We have found for instance, that outer shrink-wrap layer (582) may be a material such as cross-linked low-density polyethylene which has been inflated and irradiated. Polymeric band (580) may be similarly pre-treated fluorinated ethylene propylene polymers (FEP). Various polymers used in medical service such as PEBAX (as described above) and polyurethanes are thermoplastics which may be used in outer layer (572) as described above.

Figure 14C:
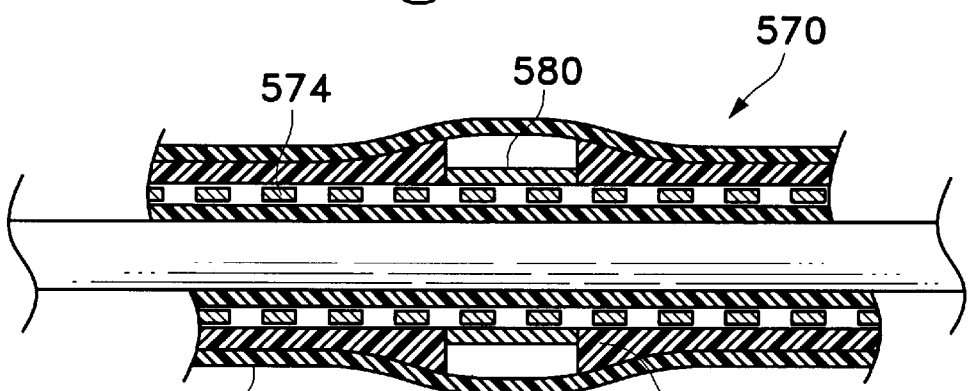

FIG. 14C shows the result of heating the catheter section (570) in the configuration shown in FIG. 14B. It is to be noted that polymeric band (580) has shrunk and is now merely to, or is at the surface of, coil or braid member (574). The material forming the outer layer has formed small bumps (584) adjacent polymeric band (580); balloon tubing (582) has maintained the general shape of the hills or flares (584) during this heating step.

Figure 14D:
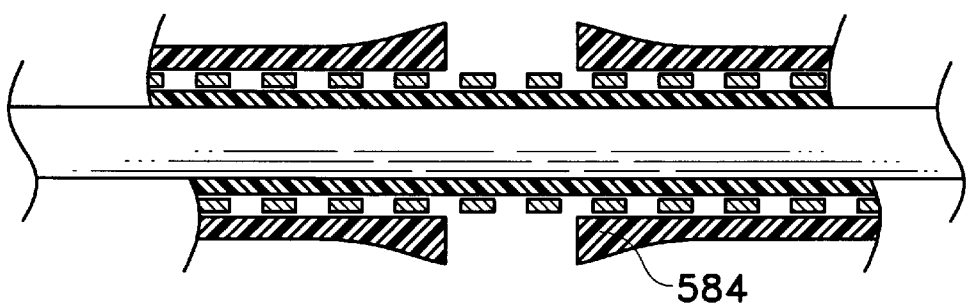

FIG. 14D shows the result of the heating step after polymeric band (580) and outer shrink-wrap tubing member (582) have been removed from the device (570). The hills or flares (584) may be seen and the site for placement of the radio-opaque band is apparent between the various sections of the flare (584).

Figure 14E:
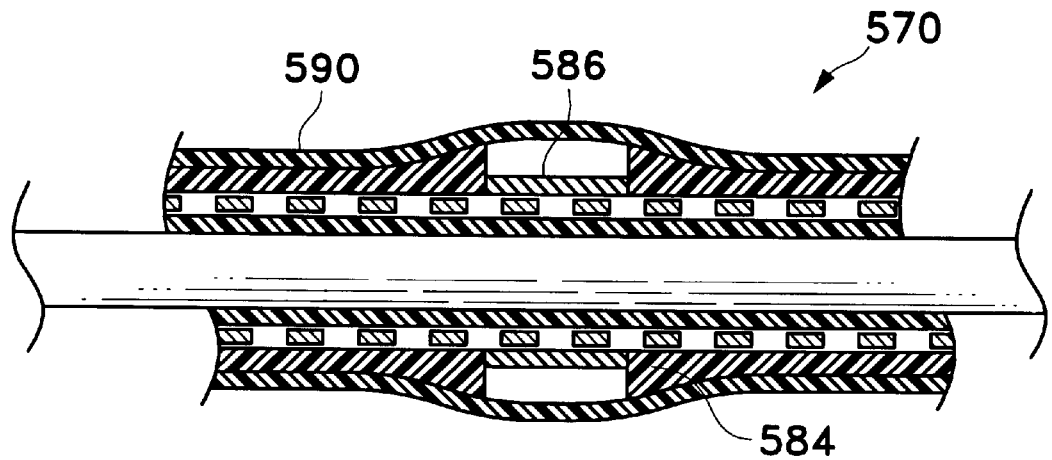

FIG. 14E shows the section (570) after the placement of a radio-opaque band (586). Another layer of shrink-wrappable tubing (590) is also depicted in place in FIG. 14E. Radio-opaque band (586) may be any of a variety of materials. It may be a split ring of a polymer having a high loading of radio-opaque fillers such as those discussed above. It may be a pair of split rings of the radio-opaque metals discussed just above. Highly preferred because of its exceptional radio-opacity is an alloy of platinum and iridium.

Figure 14F:
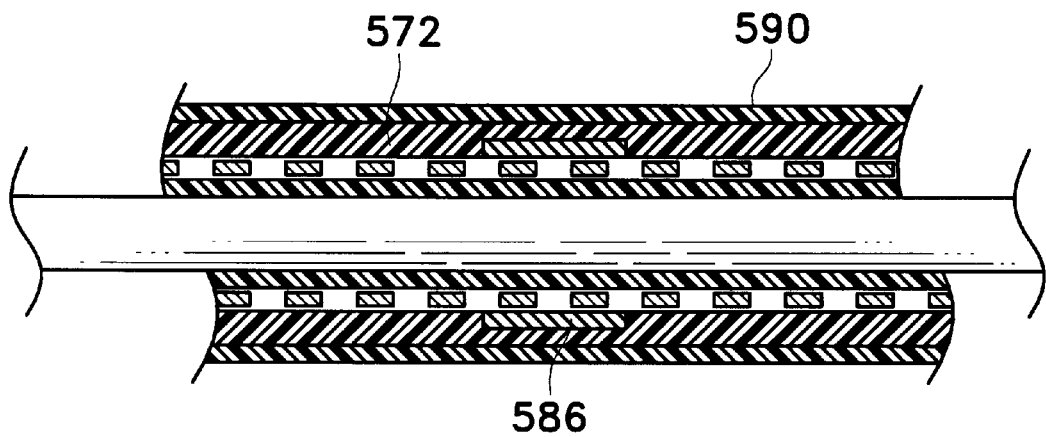

FIG. 14F shows the result of a subsequent reheating step. As a result of heating the outer shrink-wrappable tubing (590) and the thermoplastic outer layer (572), radio-opaque band of (586) has been sealed in place. The hillock or flares (584) shown in FIGS. 14C, 14D, and 14E have been eradicated by flow of the polymer over the exterior of radio-opaque band (586).

Figure 14G:
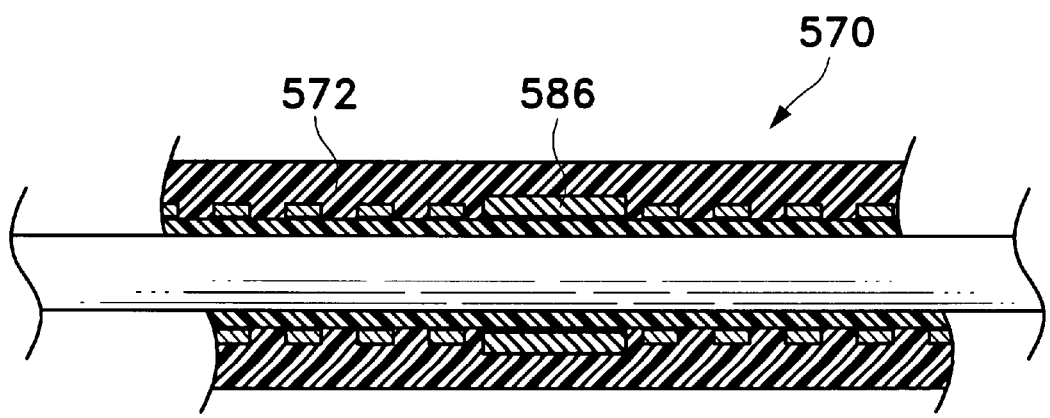

FIG. 14G shows the resulting catheter section (570) with the radio-opaque band (586) installed therein. The exterior surface of outer covering (572) may be observed to be quite smooth and without any exterior bumps. Use of this procedure, in contrast to others of which are known in the catheter production art, produces a much smoother catheter over this site. It should be noted that in FIG. 14G the inner mandrell has been removed.

Figure 15A:
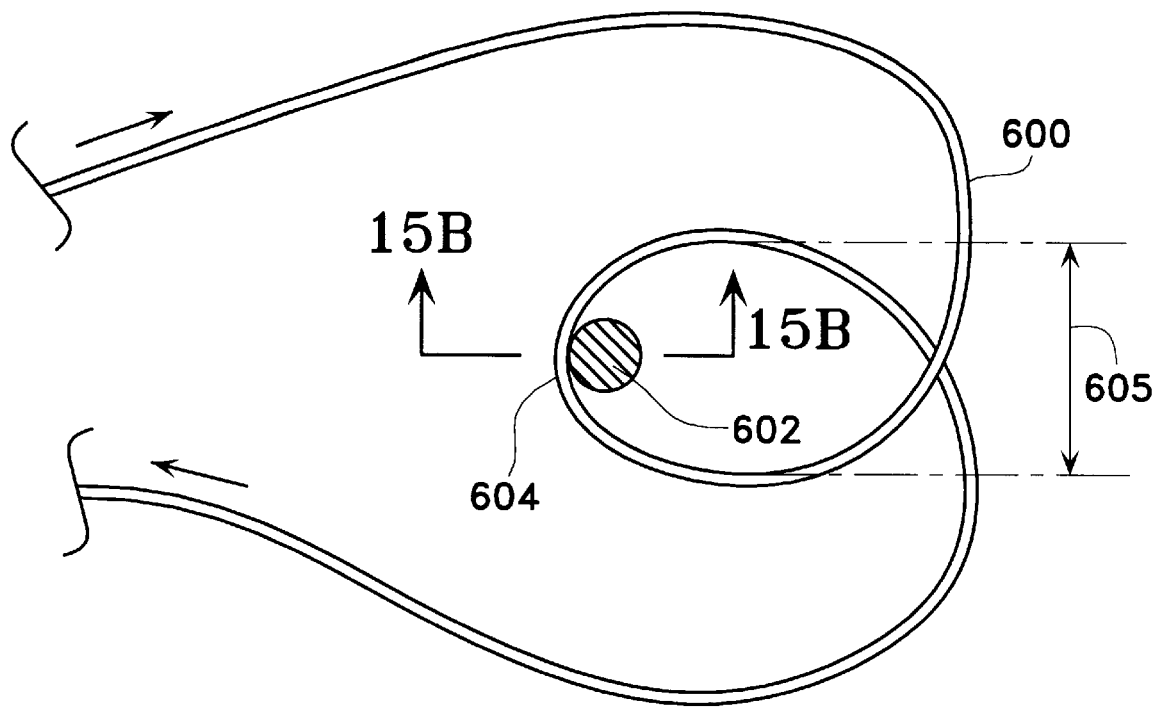
FIGS. 15A and 15B show details of methods for determining the "critical bend diameter" for a catheter.
Figure 15B:
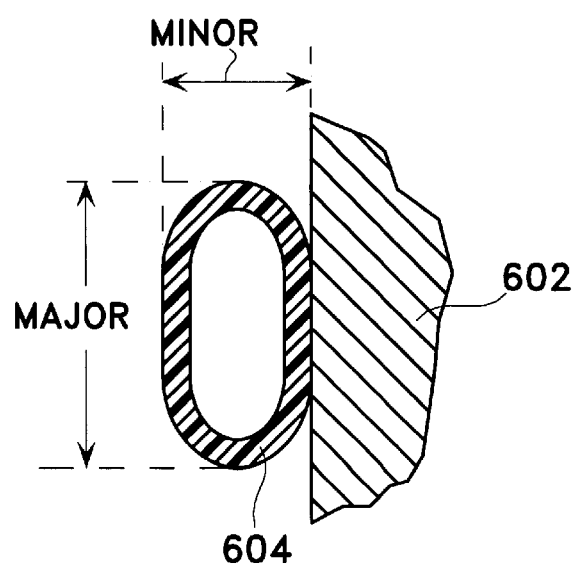

The test we utilize for critical bend diameter determination uses a test shown schematically in FIGS. 15A and 15B.

In general, as shown in FIG. 15A a catheter section (600) is placed between two plates (desirably of plastic or glass or the like for visibility) and often with an optional peg (602) to hold the catheter section (600) loop in place. The ends of the catheter are then pulled until a kink appears in the body of the catheter. The diameter (605) of the catheter loop at the occurrence of that kink is the critical kink diameter. Alternatively, the ratio of the outer diameters (major diameter:minor diameter) may be measured at apex (604). The diameter (605) of the catheter loop at the occurrence of that kink is the critical kink diameter when the ratio of outer diameters reaches a value of 1.5. FIG. 15B shows the cross section of the catheter sector at (604) and further shows the manner in which the major diameter and the minor diameter are measured. These two methods provide comparable results although the latter method is more repeatable.

EXAMPLE 1

We constructed an intravascular catheter using the concepts of this invention. The device was about 150 cm. overall and had an inner tubing member of TFE. That inner tubing member had a wall thickness of about 0.75 mil. The wall thickness of the inner liner was difficult to determine because the tubing is stretched from its original configuration. A 0.7 mil thickness of a polyurethane blend was then applied to the TFE inner lining. This subassembly (having a mandrel in its center) was then mounted in a lathe-like apparatus to add the helically wound reinforcing member. The reinforcing member was a ribbon of 304 SS having a thickness of 0.75 mil and a width of 3 mils. It was secured to the distal end using a platinum band which was about 1 mil in length. The assembly was rotated in the coil-winder to wind the ribbon from the distal end to the proximal end. At the proximal end, the direction of the ribbon wind was changed so that the ribbon was being wound towards the distal end. The ribbon was wound to the end of the catheter so that a double layer of ribbon was found from distal end to proximal end. Several sections of polymeric tubing formed of PEBAX (a thermoplastic elastomer sold by Elf Atochem North America), each having a different flexural modulus, were placed on the shaft assembly. A shrink-wrappable polyethylene tubing was then placed on the exterior of the PEBAX tubing and the assembly was heated. The polyethylene shrink-wrap pulled the PEBAX tubing down to the coil surface. The polyethylene shrink-wrap tubing was then stripped from the exterior of the assembly. The distal tip had a kink resistance of about 1.0 mm.

EXAMPLE 2

We constructed a set of five intravascular catheters using the concepts of this invention with two coils and a set of five comparative catheters having a single coil but otherwise identical.

Each device was about 150 cm. overall and had an inner tubing member of TFE. A 0.7 mil thickness of a PEBAX 55D polyether-polyamide was then applied to the TFE inner lining. This subassembly (having a mandrel in its center) was then mounted in a lathe-like apparatus to add the helically wound reinforcing members. The reinforcing members were ribbons of 304 SS (vacuum melt refined) having a thickness of 0.45 mil and a width of 3 mils. The two ribbons on the inventive catheter (one wound clockwise and one wound counterclockwise) extended from the proximal end to the distal end and had a constant pitch of 12 mils. A single coil ribbon also having a pitch of 12 mils was wound on the comparative catheter. A short bumper tip without coil was left on each distal end. Two platinum bands, each about 1 mil in length were placed 15 cm apart at the distal end. Two sections of polymeric tubing formed of PEBAX (a thermoplastic elastomer sold by Elf Atochem North America), each having a different flexural modulus—15 cm. of Shore 70A polymer at the distal end and 30 cm. of Shore 55D polymer at the midsection, the more proximal end of the midsection having an additional 15 cm. layer of Shore 55D polymer forming a transition between the distal midshaft and the proximal shaft—were placed on the shaft assembly. A 105 cm. length of Carbothane (a polyurethane polycarbonate polymer) formed the most proximal portion of the catheter shaft. A shrink-wrappable polyethylene tubing was then placed on the exterior of the tubing and the assembly was heated. The polyethylene shrink-wrap pulled the various tubing members down to the coil surface. The polyethylene shrink-wrap tubing was then stripped from the exterior of the assemblies.

Each catheter was then tested for flexibility using a Tinius-Olsen (ASTM 4809 & 2436) procedure. The test using a Tinius-Olsen device merely bends a specific length of the device using a number of specific weights and measures the resultant angular deflection. The results of the respective tests (averages of the respective sets of five catheters) are shown below in Table 1 and in FIG. 16.

| | Comparative Catheter | | | Inventive Catheter | | |
|---|---|---|---|---|---|---|
| Angular Defl. | Ave. − 3S.D. Single Coil | AVERAGE Single coil | Ave. + 3S.D. Single coil | Ave. − 3S.D. Double coil | AVERAGE Double coil | Ave. + 3S.D. Double Coil |
| 5 | 0.00958 | 0.01550 | 0.02142 | 0.00708 | 0.01300 | 0.01892 |
| 10 | 0.01478 | 0.02725 | 0.03972 | 0.01520 | 0.02400 | 0.03280 |
| 15 | 0.01775 | 0.03800 | 0.05825 | 0.02189 | 0.03250 | 0.04311 |
| 20 | 0.02776 | 0.04950 | 0.07124 | 0.02667 | 0.04000 | 0.05323 |
| 25 | 0.03092 | 0.05725 | 0.080358 | 0.02911 | 0.04650 | 0.06389 |
| 30 | 0.03413 | 0.06450 | 0.09487 | 0.03356 | 0.05275 | 0.07194 |

Figure 16:
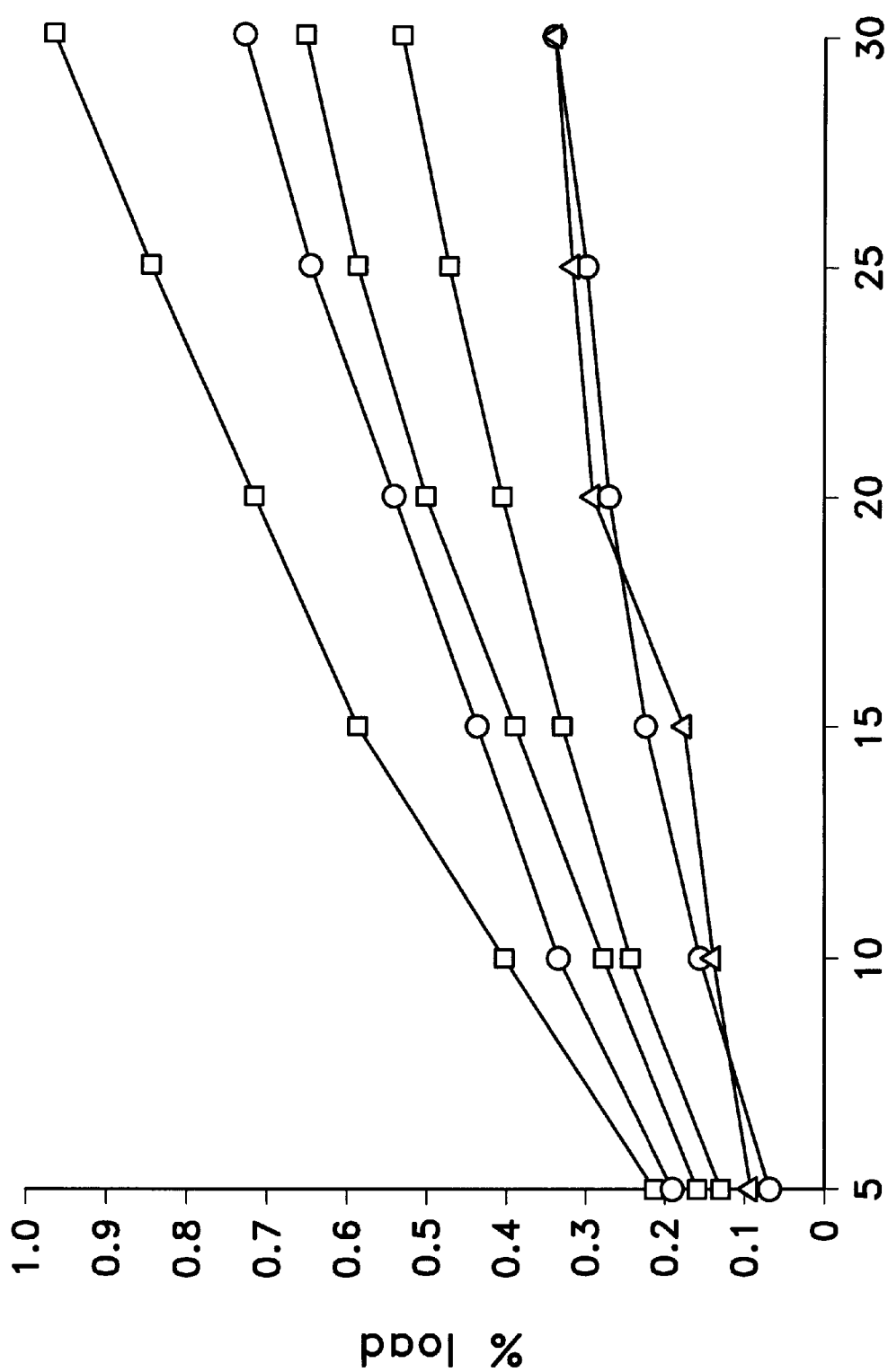
FIG. 16 is a graph of the relative stiffnesses of inventive catheter made according to this invention and a comparative catheter having but a single helical coil.

The data has been portrayed in FIG. 16 so that it should be apparent that by using a standard test such as the Tinius-Olsen ASTM procedure, that it is exceeding difficult to determine from a flexibility point of view, whether a double coil catheter made according to this inventive concept is being measured or whether a catheter having but a single coil is being measured—from a flexibility point of view. The kink resistance of the double coil device is substantially more extensive, however.

This invention has been described and specific examples of the invention have been portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

We claim as our invention:

1. A catheter comprising:
   an elongate tubular member having a proximal end and a distal end, comprising:
   a.) a tubular polymeric inner liner having a passageway defining an inner lumen and having an outer surface
   b.) at least two stainless steel ribbon reinforcing members, each said stainless steel ribbon reinforcing members having a width and thickness, one of said stainless steel ribbon reinforcing members having turns spirally wound in a first-handed direction from said proximal end to said distal end exterior to said tubular polymeric inner liner and one of said stainless steel ribbon reinforcing members having turns spirally wound in a second-handed direction from said proximal end to said distal end,
   c.) a tubular polymeric filler member between said ribbon reinforcing members and said polymeric inner liner, and
   d.) at least one exterior tubing member exterior to said ribbon reinforcing member and in contact with said tubular polymeric filler member through said turns of said at least two stainless steel ribbon reinforcing members.

2. The catheter of claim 1 wherein said stainless steel ribbon reinforcing members have a thickness of 0.25 to 1.50 mils.

3. The catheter of claim 1 wherein said stainless steel ribbon reinforcing members have a width of 1.0 to 8.0 mils.

4. The catheter of claim 1 wherein at least one of the stainless steel ribbon reinforcing members has a pitch which varies between the proximal end and distal end.

5. The catheter of claim 1 wherein the tubular polymeric inner liner is polytetrafluoroethylene.

6. The catheter of claim 1 wherein the exterior tubing member comprises a polymer selected from the group consisting of polyurethane, polyethylene, ethylvinylacetate, polyethylene terephthalate, polvinylchloride, polyamides, polyethers, and their mixtures and block and random copolymers.

7. The catheter of claim 1 wherein the exterior tubing member comprises a polymer comprising a polyamide-polyethers block copolymer.

8. The catheter of claim 1 where exterior tubing member contains a radio-opacifier.

9. The catheter of claim 1 wherein the tubular polymeric filler member comprises a polymer selected from the group consisting of polyurethane, polyethylene, ethylvinylacetate, polyethylene terephthalate, polvinylchloride, polyamides, polyethers, and their mixtures and block and random copolymers.

10. The catheter of claim 1 wherein the tubular polymeric filler member comprises a polymer comprising a polyamide-polyethers block copolymer.

11. The catheter of claim 1 wherein the tubular polymeric filler member polymer contains a radio-opacifier.

12. The catheter of claim 1 wherein the tubular polymeric inner liner contains a radio-opacifier.

13. The catheter of claim 1 further comprising a proximal helically wound ribbon member located proximally on said elongate tubular member.

14. The catheter of claim 1 wherein each of said at least one stainless steel ribbon reinforcing members is wound of a single continuous ribbon.

15. The catheter of claim 1 wherein the exterior tubing member comprises more than one tubing section.

16. The catheter of claim 1 further comprising a nose section distally located on said elongate tubular member and distal of said at least one stainless steel ribbon reinforcing members.

17. The catheter of claim 16 wherein said nose section has a length and a diameter and wherein said length is no more than 10 times its diameter.

18. The catheter of claim 1 wherein said elongate tubular member has an axis extending from said distal end to said proximal end and at least one of said at least one stainless steel ribbon reinforcing members is wound at an angle of 10°–15° of said axis.

19. The catheter of claim 1 further comprising a guidewire placed interior to and in slideable position to said inner lumen.

* * * * *